(12) United States Patent
Balázs et al.

(10) Patent No.: US 6,258,107 B1
(45) Date of Patent: Jul. 10, 2001

(54) APPARATUS FOR CONNECTING A VARIETY OF SURGICAL INSTRUMENTS TO AN OPERATING CONTROL DEVICE

(75) Inventors: Matthias Balázs, Grafrath; Ulrich Hagn, Wessling, both of (DE)

(73) Assignee: Deutsches Zentrum für Luft-und Raumfahrt e.v., Bonn (DE)

( * ) Notice: Subject to any disclaimer, the term of this patent is extended or adjusted under 35 U.S.C. 154(b) by 0 days.

(21) Appl. No.: 09/375,517

(22) Filed: Aug. 17, 1999

(30) Foreign Application Priority Data

Aug. 17, 1998 (DE) ............................................. 198 36 950

(51) Int. Cl.[7] .................................................... A61B 17/04
(52) U.S. Cl. ...................... 606/153; 606/139; 227/175.1; 227/179.1
(58) Field of Search ................................... 227/175–180; 606/139, 1, 153

(56) References Cited

U.S. PATENT DOCUMENTS

| | | |
|---|---|---|
| 4,207,898 | 6/1980 | Becht . |
| 4,606,343 | 8/1986 | Conta et al. ..................... 227/DIG. 1 |
| 5,104,025 | 4/1992 | Main et al. . |
| 5,411,508 * | 5/1995 | Bessler et al. ........................ 606/153 |
| 5,533,661 | 7/1996 | Main et al. ........................ 227/176.1 |
| 5,669,918 | 9/1997 | Balazs et al. . |
| 5,718,360 * | 2/1998 | Green et al. ........................ 227/179.1 |
| 5,839,639 * | 11/1998 | Sauer et al. ........................ 227/175.1 |
| 5,860,581 * | 1/1999 | Robertson et al. ............... 227/179.1 |
| 6,050,472 * | 4/2000 | Shibata .............................. 227/179.1 |
| 6,053,390 * | 4/2000 | Green et al. ....................... 227/179.1 |

FOREIGN PATENT DOCUMENTS

| | | |
|---|---|---|
| 2851144 | 12/1981 | (DE) . |
| 691 08 8390 | 11/1995 | (DE) . |
| 195 09 115 | 9/1996 | (DE) . |

* cited by examiner

Primary Examiner—Gary Jackson
(74) Attorney, Agent, or Firm—Browdy And Neimark

(57) ABSTRACT

For connecting a variety of surgical instruments for both minimally invasive surgery and for application in open surgery a push-button fastener is provided at the proximal end of the instrument to be connected in each case at the distal end of a shank part of an operating control device. Furthermore, for connecting and actuating the function elements of the instrument connected in each case a mandrel assembly is provided at the proximal end of the instrument, the mandrel assembly being in turn mounted on and latched to a receiving part at the distal end of an adjuster mechanism actuatable by the operating control means. Preferably, the mandrel assembly is tubular pin body slotted at its proximal end, having splined portions which is mounted on and latched to a contact pin guided and positioned in the shank part.

19 Claims, 15 Drawing Sheets

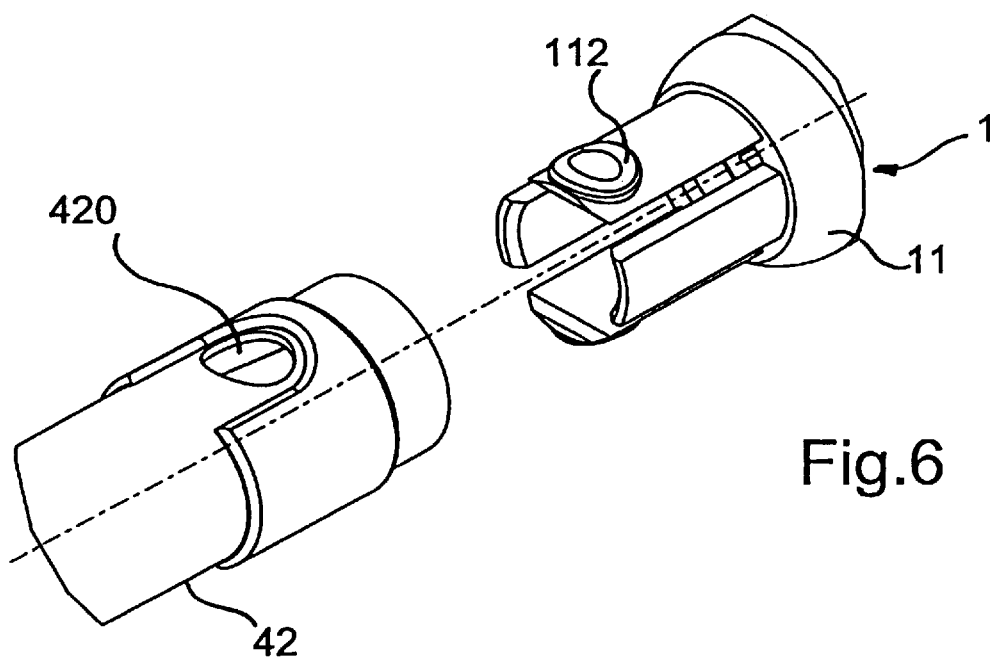
Fig. 6
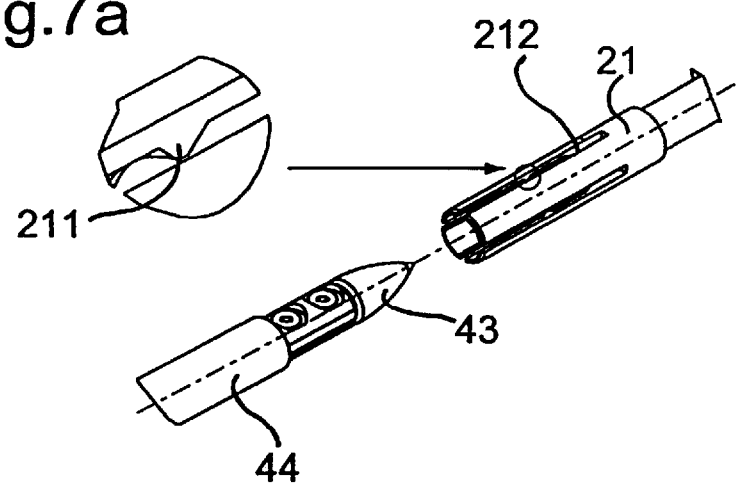
Fig. 7a
Fig. 7
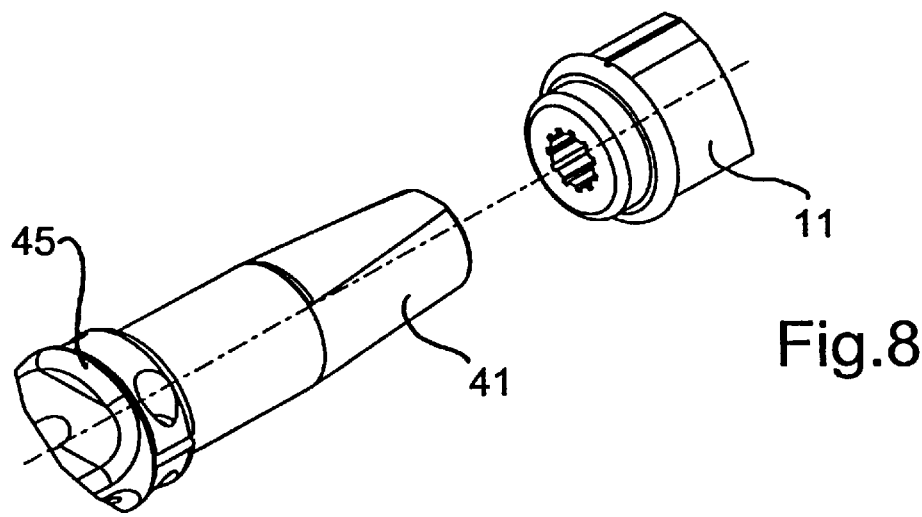
Fig. 8

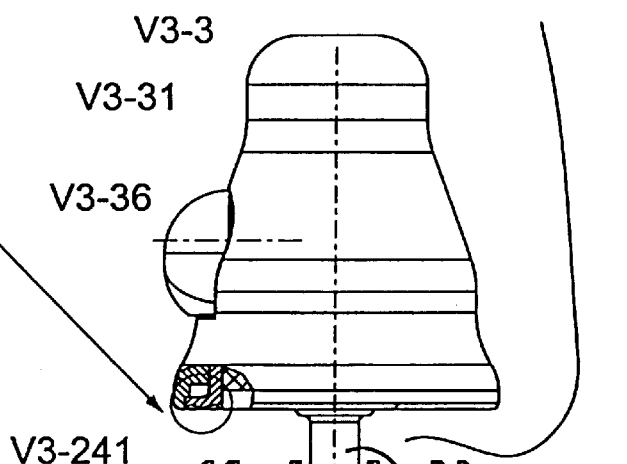
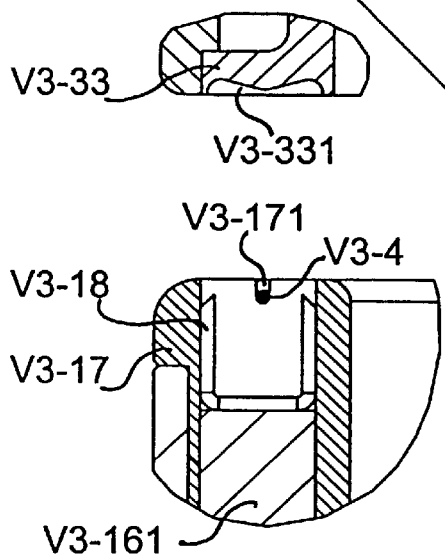
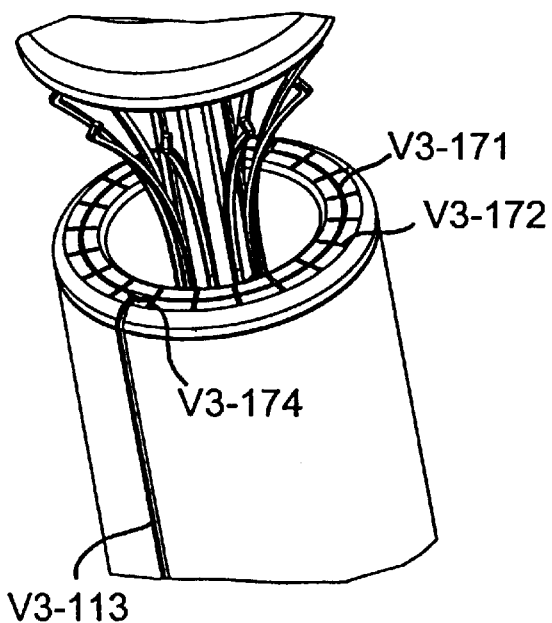
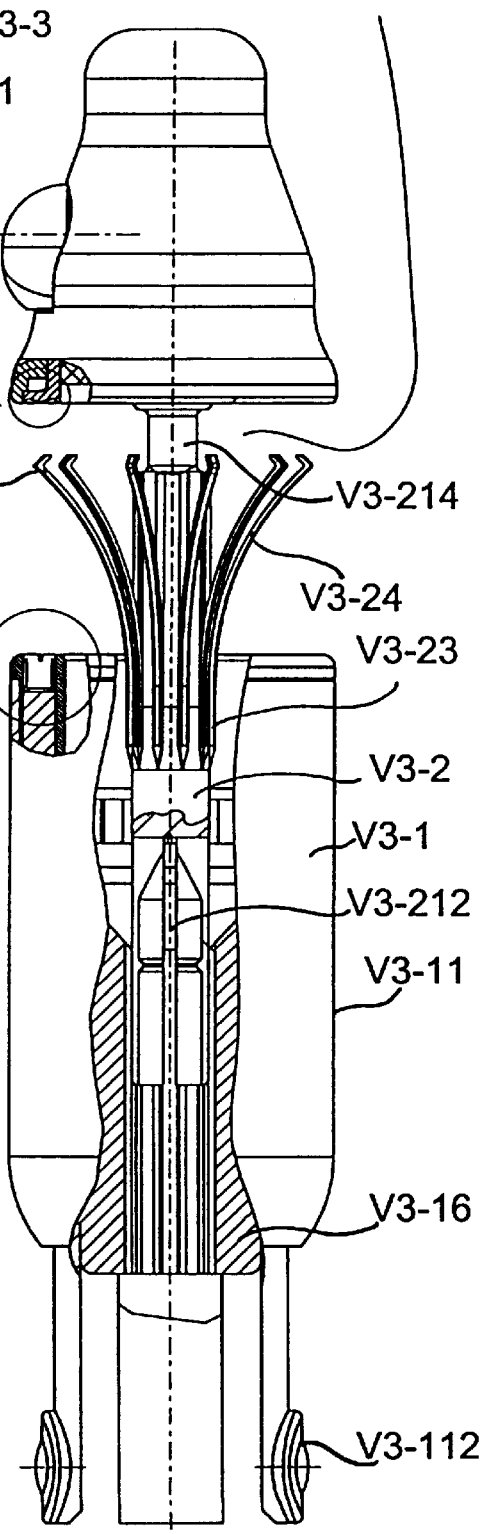
Fig.15b
Fig.15c
Fig.15d
Fig.15a

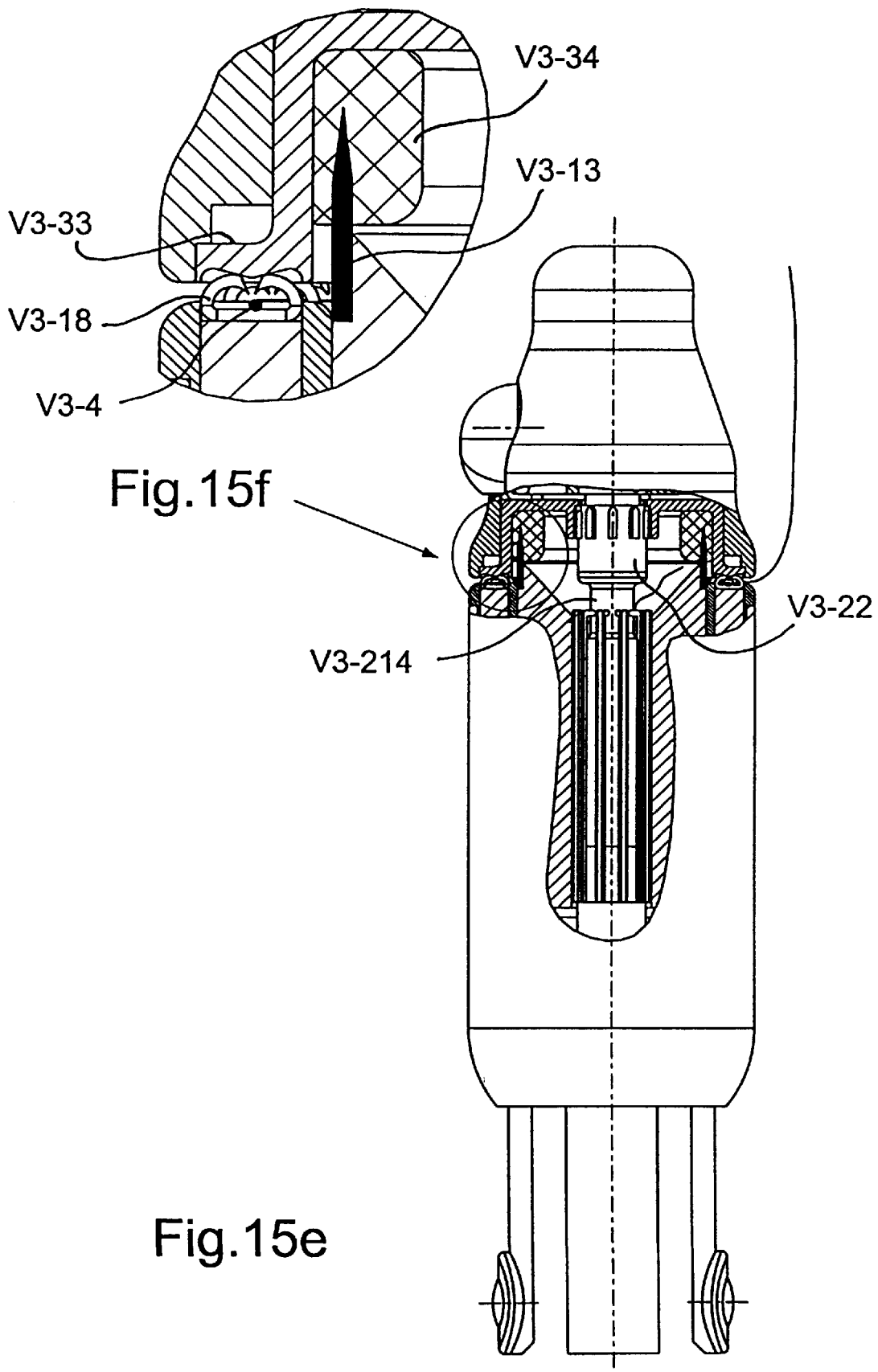

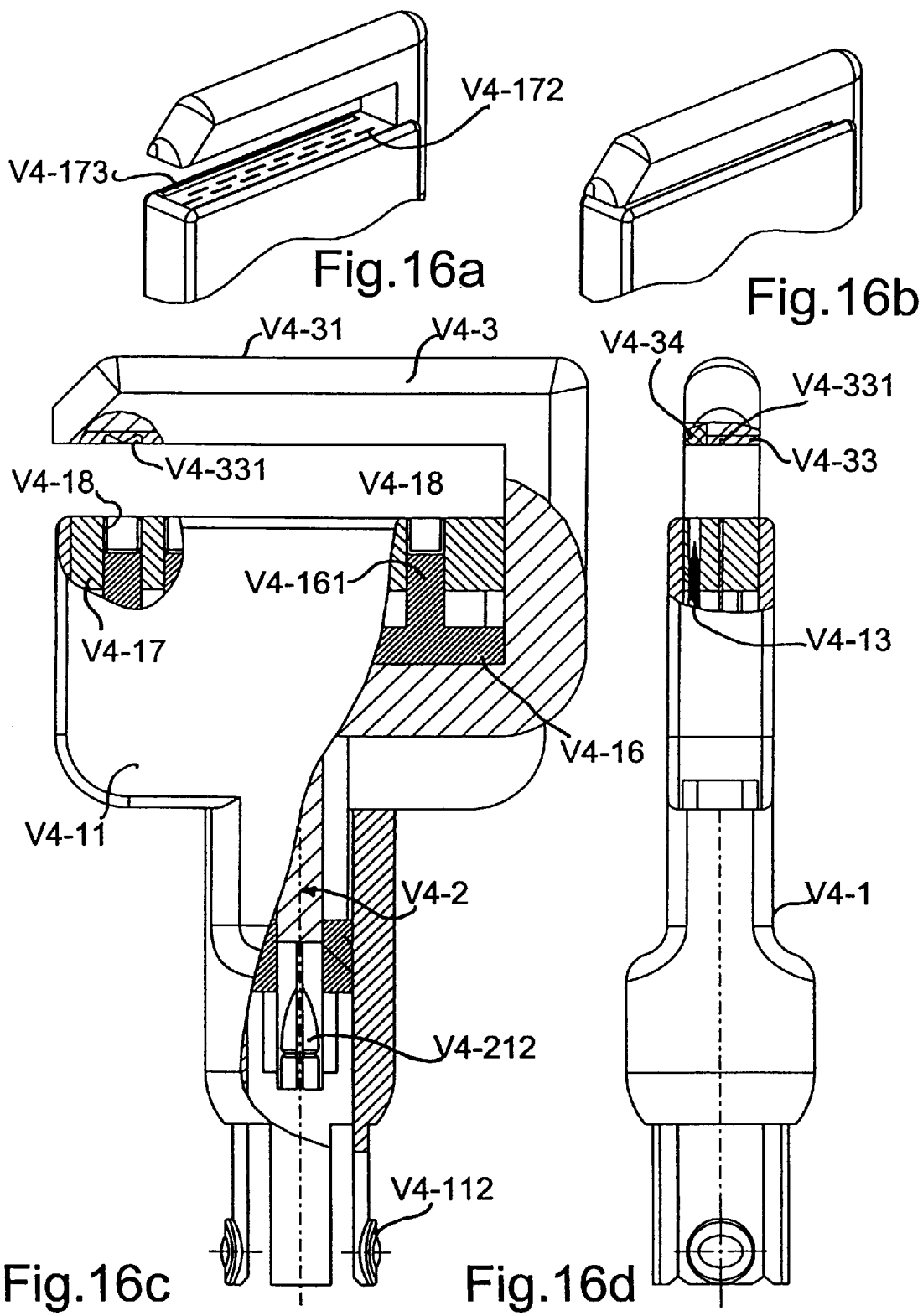

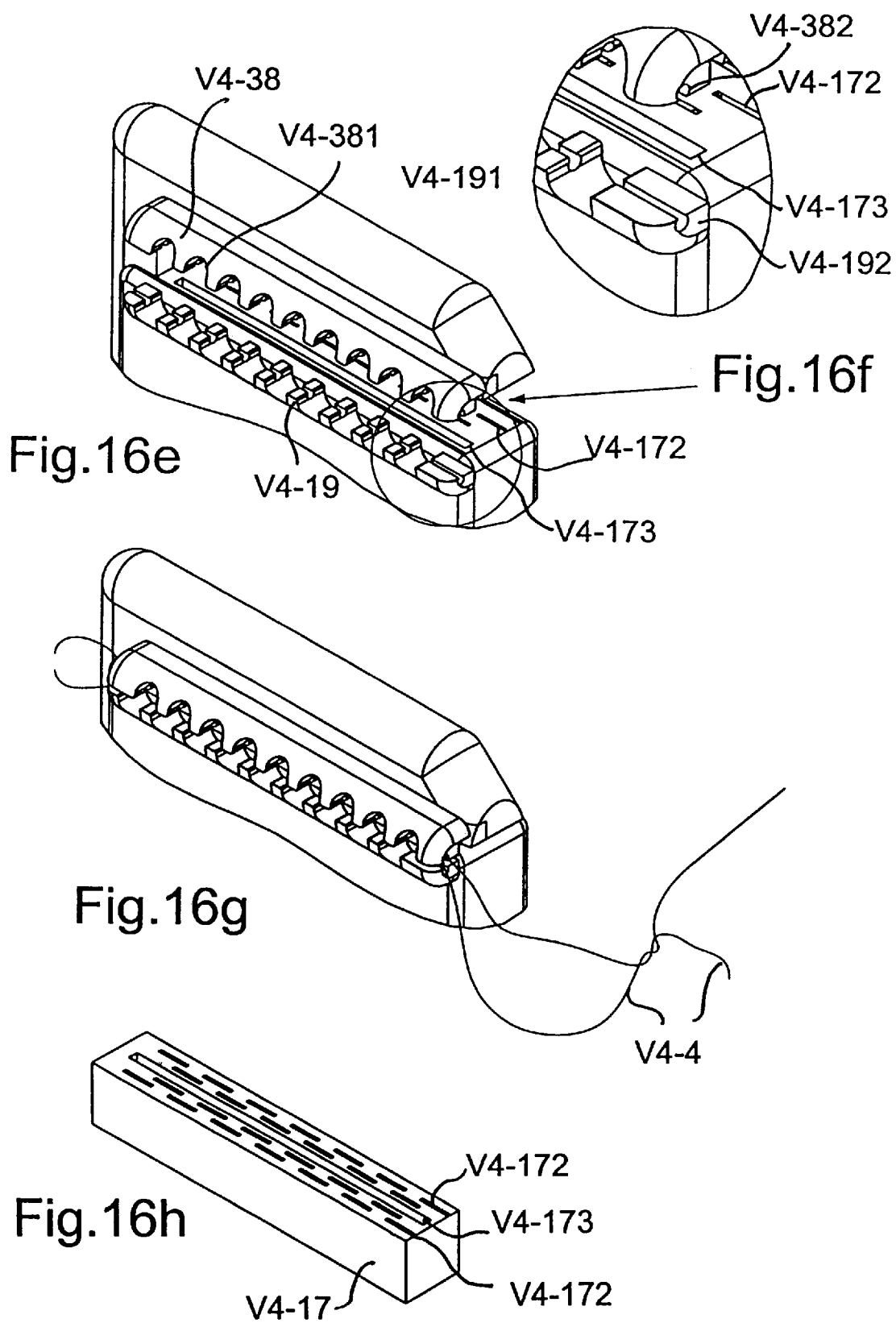

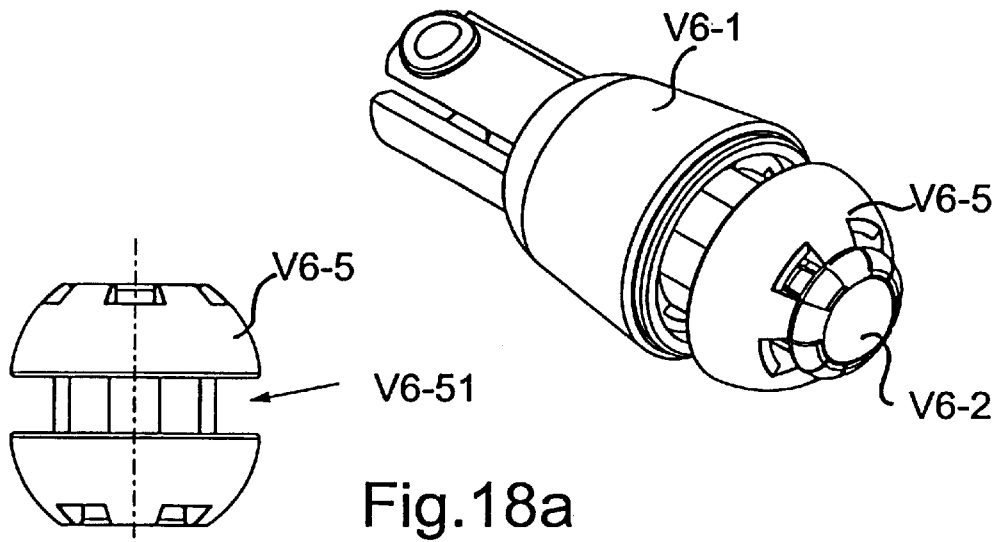
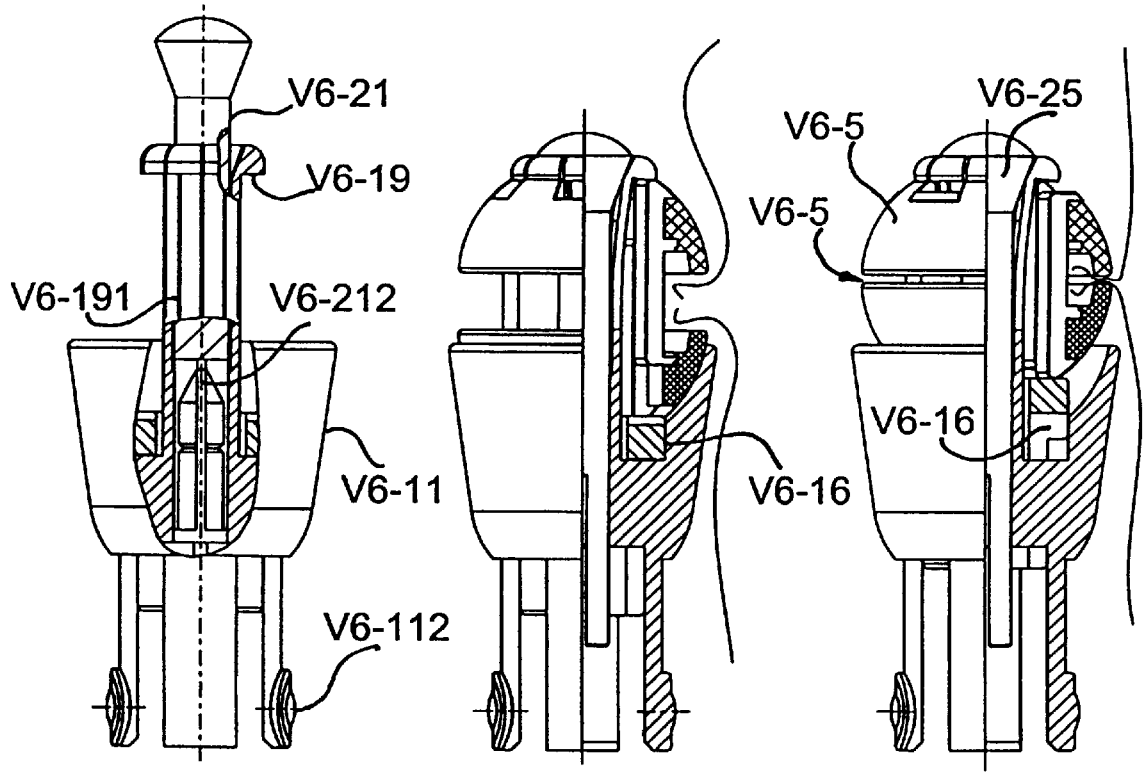
Fig.18a
Fig.18b    Fig.18c    Fig.18d

APPARATUS FOR CONNECTING A VARIETY OF SURGICAL INSTRUMENTS TO AN OPERATING CONTROL DEVICE

TECHNICAL FIELD AND BACKGROUND OF THE INVENTION

The invention relates to an apparatus for connecting a variety of surgical instruments to an operating control device.

Disclosed, for example, by U.S. Pat. No. 4,573,468 is a circular stapling device from which the head unit may be removed as a whole. Connecting the head unit to an operating control part on this stapling device is achieved by a complicated bayonet lock. Furthermore, the clincher insertion head needs to be screwed onto/from this known instrument which is a nuisance and time-consuming.

As it reads from U.S. Pat. No. 5,533,361 a head part of the surgical instrument is positively connected by a crimped tube stiffly and non-separably to a shank part of the operating control means. In U.S. Pat. No. 4,606,343 too, it reads that a shank tube of the operating control device and a head part of the surgical instrument are likewise fixedly connected to each other. Replacing any parts of the surgical instrument is thus not provided for.

SUMMARY OF THE INVENTION

It is thus the object of the invention to configure a variety of surgical instruments so that they can be quickly replaced whilst retaining satisfactory operating control of the element in each case, and that furthermore as many function elements as possible of the various instruments are reusable.

In accordance with the invention, for connecting a variety of surgical instruments for both minimally invasive surgery and for application in open surgery a push-button fastener is provided at the proximal end of the instrument to be connected in each case at the distal end of a shank part of an operating control device. Furthermore, for connecting and actuating the function elements of the instrument connected in each case a mandrel assembly is provided at the proximal end of the instrument which is mounted on a receiving part at the distal end of an adjuster mechanism actuatable by the operating control means.

In accordance with the invention the mandrel assembly is preferably a tubular pin body slotted at its proximal end, having splined portions which is mounted on a contact pin guided and positioned in the shank part and connected to the adjustmer mechanism of the operating control means.

Unlike the complicated need to screw the clincher insertion head onto the circular stapling device as disclosed by U.S. Pat. No. 4,573,468 the head unit is connected by the solution in accordance with the invention via a simple push button fastener to the distal end of the shank part of the operating control means. In addition, connection of the clincher insertion head for instance of a circular stapling device is achieved via a latch fastener. In accordance with the invention a variety of instruments can thus be speedily and intuitively connected to the shank part of an operating control means and, at the same time, salient function elements of the surgical instrument concerned to be connected via a mandrel provided at the distal end of the shank part of the operating control means.

BRIEF DESCRIPTION OF THE DRAWINGS

The invention will now be detailed by way of preferred embodiments with reference to the drawings in which:

FIG. 2a depicting those of the staple cartridge assembly, FIG. 2b those of the mandrel assembly and FIG. 2c those of the clincher insertion head assembly.

FIG. 6 is a magnified perspective illustration of the push button fastener applied to the distal end of a shank part including a button mechanism assigned thereto at the proximal end of the head unit;

FIG. 7 is a perspective illustration of a section at the distal end of a contact pin and a mount on a mandrel;

FIG. 7a is a detail of the contact pin shown greatly magnified;

FIG. 8 is an illustration of a modified version of the distal end of a shank part and a proximal end of a head unit adapted thereto;

FIG. 15a is a partly perspective illustration and partly section view of an embodiment of a purse string suture applicator;

FIG. 15b is a magnified section view of a detail of the clincher insertion head of the purse string suture applicator as shown in FIG. 15a;

FIG. 15c is likewise a magnified section view of a detail of a staple cartridge with inserted staple;

FIG. 15d is a perspective illustration of the staple cartridge with inserted suture loop as seen from above;

FIG. 15e is a section view in part of the purse string suture applicator with the clincher insertion head retracted and stapling implemented;

FIG. 15f is a section view on a greatly magnified scale of a suture stapled to one bowel end with the scalpel knife extended;

FIG. 16a is a perspective illustration of a staple cartridge of a linear stapler with extended clincher insertion head as seen from above;

FIG. 16b is an illustration of the staple cartridge as shown in FIG. 16a with the clincher insertion head retracted;

FIG. 16c is a side view partly sectioned of a first embodiment of a linear stapler with the clincher insertion head extended;

FIG. 16d is a frontal view partly sectioned of the linear stapler with the clincher insertion head extended;

FIG. 16e is a perspective illustration of the stapling portion of the linear stapler with the clincher insertion head extended and an adapter connected;

FIG. 16f is a detail illustration of the stapling portion as shown in FIG. 16e;

FIG. 16g is a perspective illustration of a closed stapling portion;

FIG. 16h is a perspective illustration of a further embodiment of the staple cartridge as seen from above;

FIG. 18a is perspective illustration of an anastomosis ring applicator as viewed overall;

FIG. 18b is a side view of the anastomosis applicator as shown in FIG. 15a, shown partly in section, with an open anastomosis ring;

FIG. 18c is illustration partly in section of an anastomosis applicator as shown in FIG. 18b with the mounted anastomosis ring open and showing the inerted ends of the hollow organ represented schematically, and FIG. 18d is an illustration partly in section of the anastomosis applicator corresponding to that as shown in FIG. 18c with the anastomosis ring closed.

DETAILED DESCRIPTION

Figure 1:
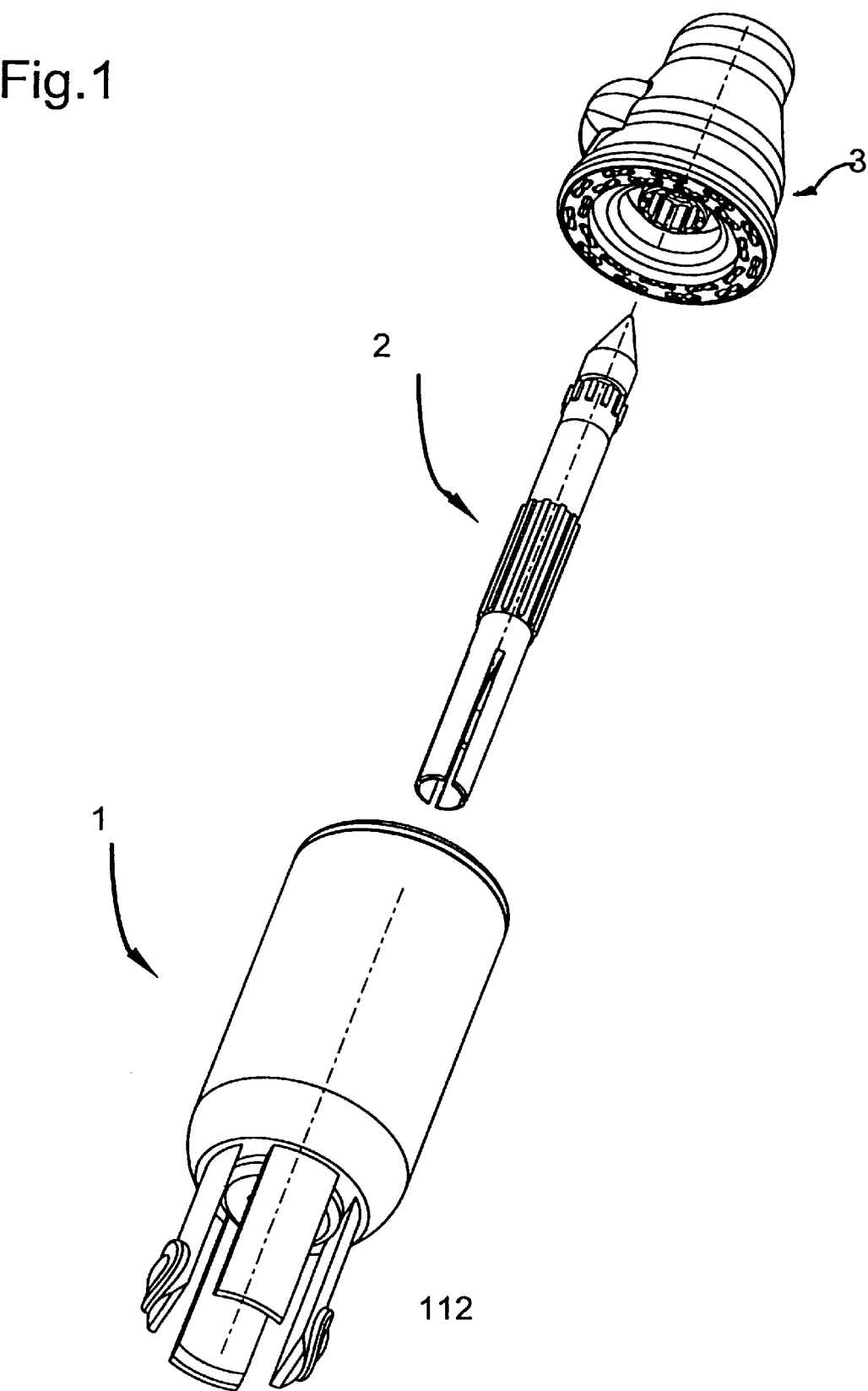
FIG. 1 is a perspective illustration of the three main assemblies of a head unit.

Referring now to FIG. 1 there is illustrated how a head unit of circular stapling device is split up into three assemblies, namely a staple cartridge assembly 1, a mandrel assembly 2 and a clincher insertion head assembly 3.

Figure 2A:
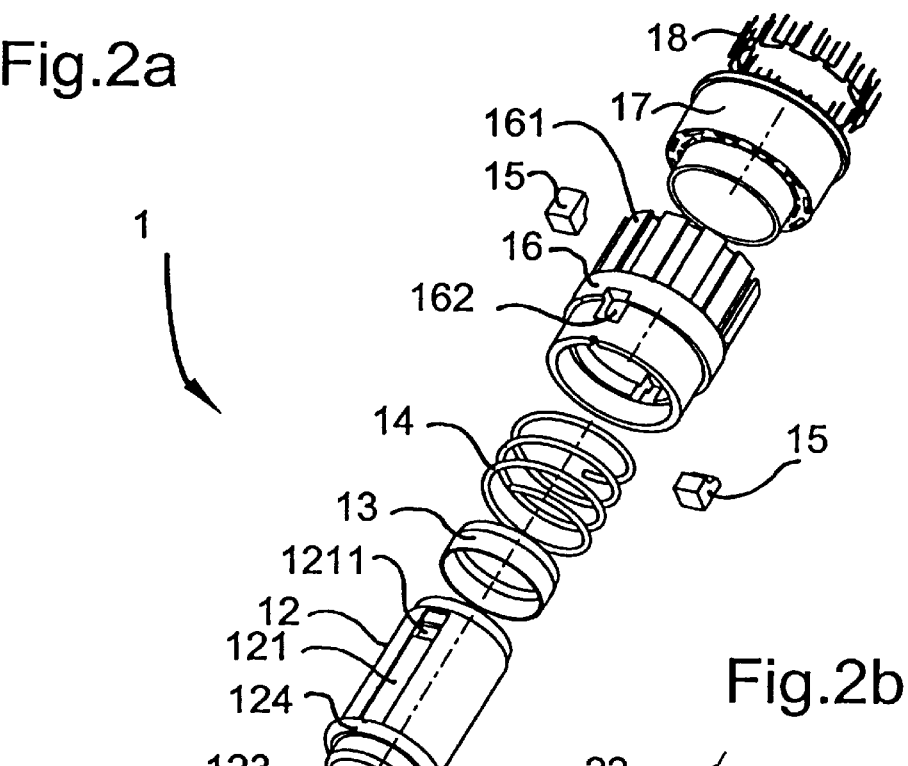
FIGS. 2a to 2c are exploded views each likewise in a perspective illustration of the individual parts of the three main assemblies of the head unit as shown in FIG. 1, i.e.

Referring now to FIG. 2a it is evident that the staple cartridge 1 is accommodated in a housing 11 of a head unit of the circular stapling device which is connected via a push button fastener 112 to a shank tube 42 (FIG. 4) of the stapling device. Arranged concentrically in a staple cartridge 17 connected to the housing 11 are U-shaped staples 18 in at least one staple chute 172, plungers 161 of a staple ejector 16 mounted axially shiftable in the housing 11 being suitably oriented relative to the staple chute(s) 172.

Mounted axially shiftable in the housing 11 of the head unit is likewise a scalpel holder 12 with mounted scalpel 13.

Scalpel holder 12 and staple ejector 16 are connected to each other via coupling elements 15. By means of a spring 14 supporting the scalpel holder 12 at the raised face 124 against the staple ejector 16 the scalpel holder 12 together with the scalpel 13 is retracted back into the housing 11 after stapling and preferably an excision has been performed.

Figure 2B:
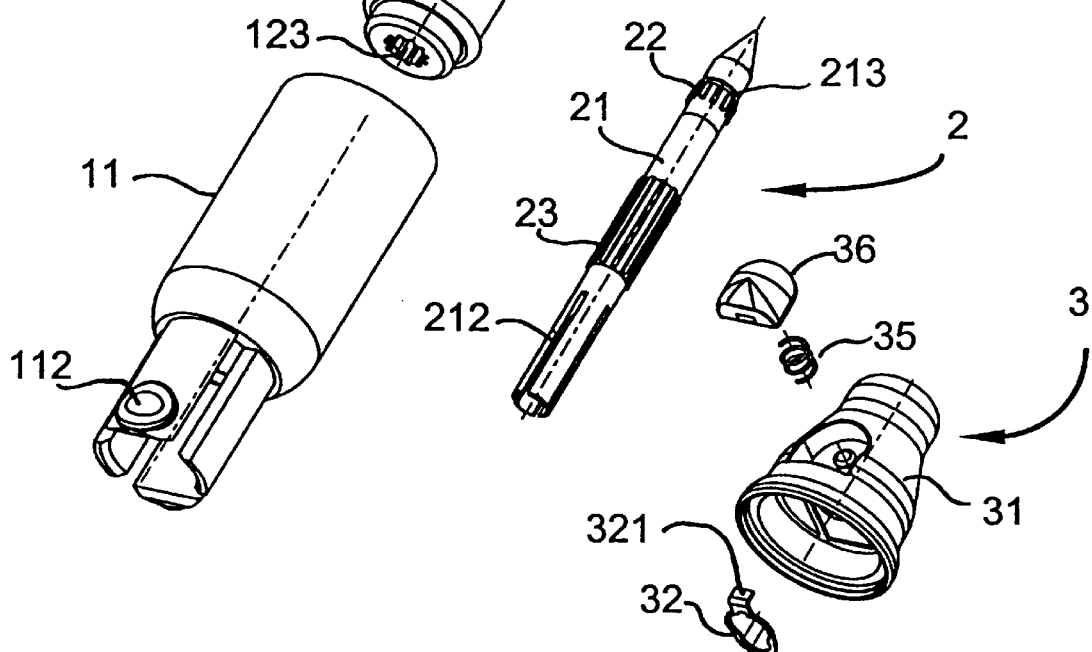

Referring now to FIG. 2b it is evident that a pin body 21 of the mandrel 2 has a tubular slotted end 212 which is mountable on a contact pin 43 of a clincher insertion head actuator mechanism 44 (see FIG. 7) of the stapling device, a circumferential groove of the contact pin 43 engaging a circumferential raised face 211 (FIG. 7a) of the inner contour of the pin 21.

In adjusting a tissue gap the contact pin 43 with the mandrel 2 is drawn into the interior of the shank tube 42 by means of the clincher insertion head adjusting mechanism 44 of the stapling device, as a result of which the slotted end 212 of the mandrel 2 is located within a barrelled pressure part 41 of the stapling device, thus arresting the connection of the contact pin 43 with the mandrel 2.

Figure 2C:
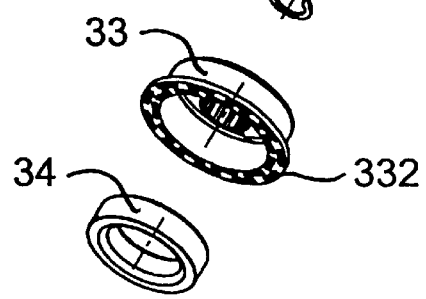
Figure 3:
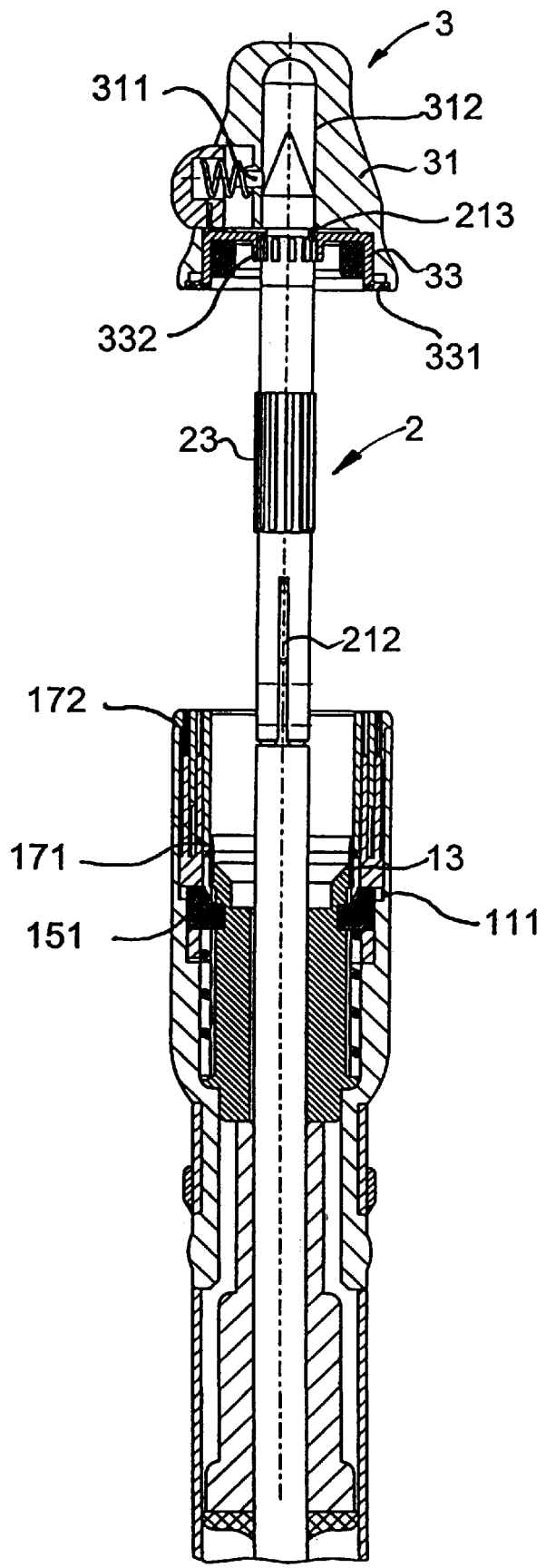
FIG. 3 is a section view of the head unit fitted to the shank with the clincher insertion head extended.

Splines 23 and 22 respectively align the mandrel 2 rotatively with reference to the splines 123 of the scalpel holder 12 and the splines 332 of a staple anvil 33 (FIG. 2c) respectively, thus assuring that the staple chutes 172 of the cartridge 17 are precisely aligned relative to the staple clinching grooves 331 of the anvil 33 (see FIG. 3, top).

Figure 5:
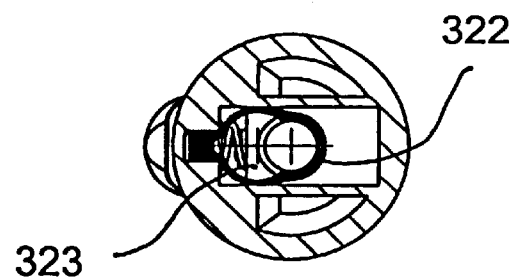
FIG. 5 is a section view through the clincher insertion head along a line 5—5 as shown in FIG. 4.

At the distal end of the mandrel 2 the clincher insertion head 2 is releasably connected, the smaller inner diameter 322 (FIG. 5) of a latching element 32 thereby engaging a corresponding groove 213 of the mandrel 2 (FIG. 2b). To release the connection between the mandrel 2 and the clincher insertion head 3 an operating control button 36 needs to be actuated to overcome the spring force of a spring 35 centered on a spigot 311 of a domed cap 31. In this arrangement the latching element 32 attached by a nose 321 in the operating control button 36 is displaced so that the larger diameter 323 of the latching element 32 is aligned in the longitudinal axis of the mandrel 2.

The diameter 323 is dimensioned somewhat larger than the outer diameter of the mandrel 2 or of a pilot hole 312 so that the mandrel in this position can be extracted from the clincher insertion head 3. The clincher insertion head 3 comprises the staple clinching grooves 331 for clinching the staples 18 as well as a ring 34 preferably made of teflon serving as the cutter counterpart for the scalpel 13 so that during the stapling action an axial force is exerted by the barrelled pressure part 41 on the scalpel holder 12.

Referring now to FIG. 6 there is illustrated in perspective a push button fastener 112 provided at the proximal end of the housing 11 of the head unit and comprising push buttons 112 seated pliantly. The push buttons 112 engage corresponding radial holes 420 in a shank tube 42.

Referring now to FIG. 7 there is illustrated in perspective the slotted end 212 of the pin body 21. As evident from the cartridge detail illustration in FIG. 7a a circumferential raised face 211 on the inner contour of the slotted tubular end 212 engages a corresponding groove in the contact pin 43 of a clincher insertion head adjusting mechanism 44 (not shown) of a operating control part.

Referring now to FIG. 8 there is illustrated part of the stapling mechanism 45 of the operating control part which translates into a barrelled pressure part 41 by means of which a compressive force is transferred as an axial pressure force into the body of a head unit.

Figure 9A:
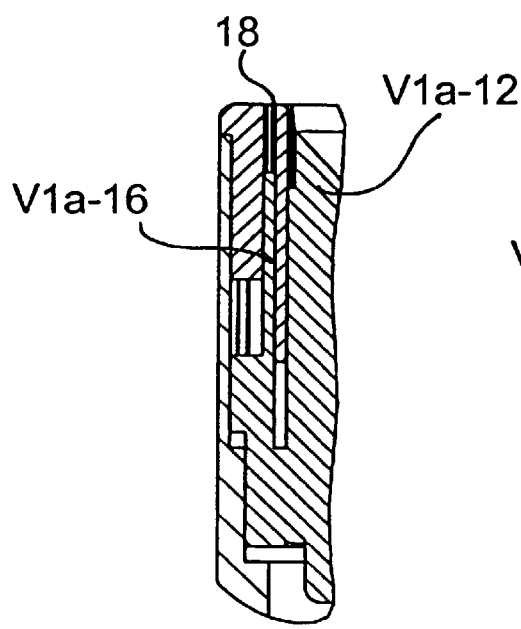
FIGS. 9a and 9b are partial section views of a scalpel holder and a staple ejector fixedly coupled thereto, i.e. shown retracted in FIG. 9a and shown extended in FIG. 9b.
Figure 9B:
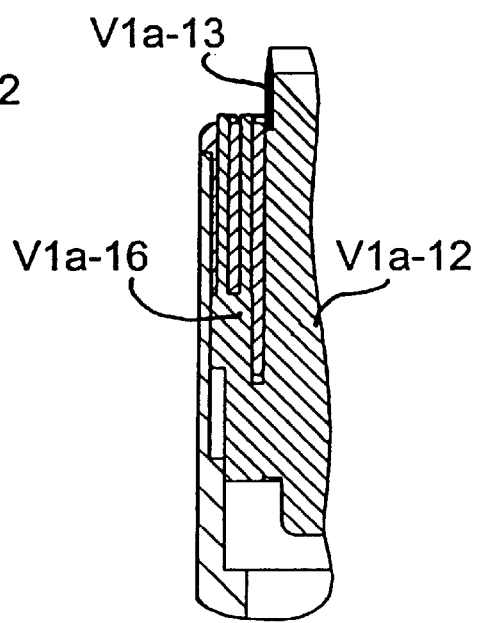

Referring now to FIGS. 9a and 9b there is illustrated a first embodiment identified as variant 1a in which scalpel holder V1a-12 and staple ejector V1a-16 are fixedly coupled, i.e. stapling and excision occurring simultaneously. In a stapling action the unit comprising scalpel holder V1a-12 and staple ejector V1a-16 is displaced axially in the housing 11 of the head unit (FIG. 9b), resulting in the staples 18 being ejected from their chutes and clinched in the staple clinching grooves 331 of the anvil 33. At the same time the circular scalpel V1a-13 trims the protruding edge of tissue.

In all embodiments as described in the following stapling is done prior to the excision. In the embodiment modified accordingly as shown in FIG. 2a to FIG. 4 as well as in FIGS. 10a and 10b, thus identified as variant V1b, and involving a linear-sensitive coupling action the staple ejector V1b-16 is connected to the scalpel holder V1b-12 by at least one coupling element 15 (FIG. 2a). This at least one coupling element 15 is seated in a window 162 of the staple ejector 16 as well as in a recess 1211 of a guiding groove 121 of the scalpel holder 12. On commencement of stapling staple ejector V1b-16 and scalpel holder V1b-12 are moved in common (FIG. 3).

Figure 4:
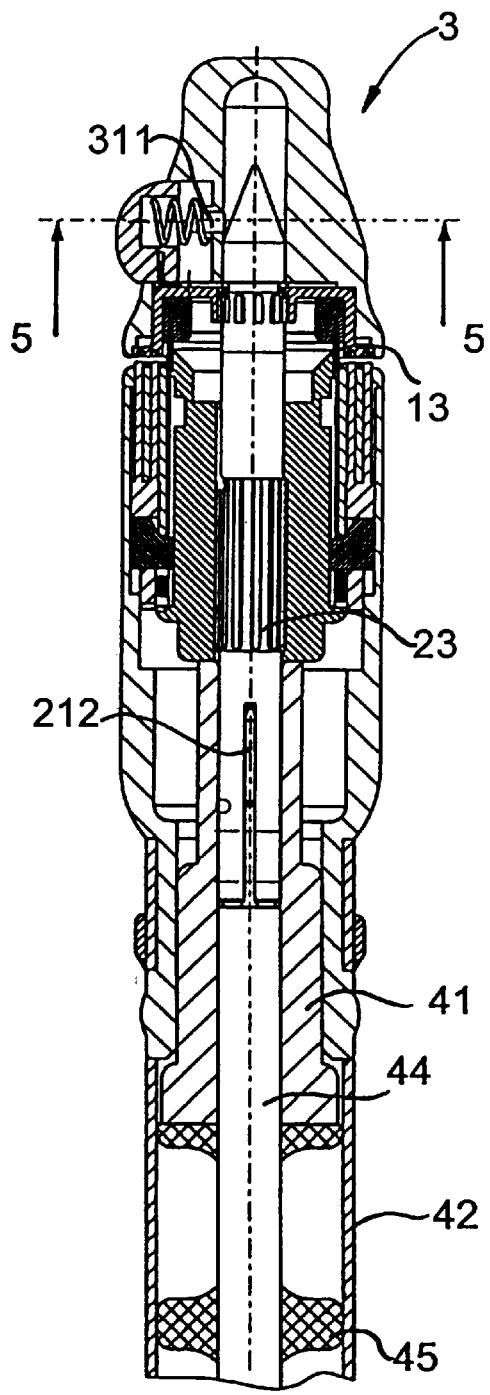
FIG. 4 is likewise a section view of the head unit fitted to the shank but with the clincher insertion head retracted and stapling implemented.

After a predetermined stapling travel the configuration of an inner contour 111 of the housing 11 enables the coupling elements 15 to be radially displaced, as a result of which a ramp 151 (FIG. 3) on each coupling element 15 comes up against a raised face 171 in the staple cartridge 17 so that the coupling element 15 is displaced radially outwards until it no longer engages the scalpel holder 12, thus subsequently resulting in staple ejector 16 and scalpel holder 12 being decoupled, after which the scalpel holder 12 travels alone to implement the excision (see FIG. 4).

Figure 10A:
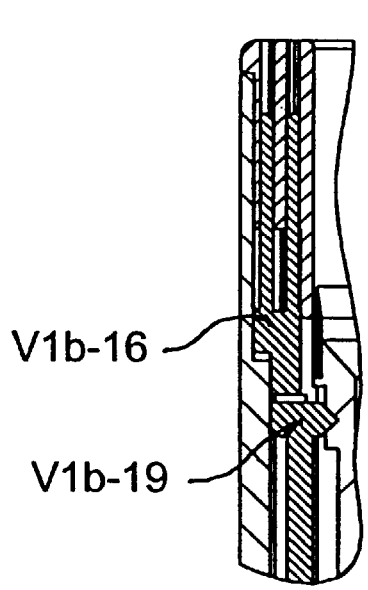
FIGS. 10a and 10b are partial section views of a first embodiment of the scalpel holder and of a staple ejector connected thereto via a coupling element, i.e. shown retracted in FIG. 10a and shown extended in FIG. 10b.
Figure 10B:
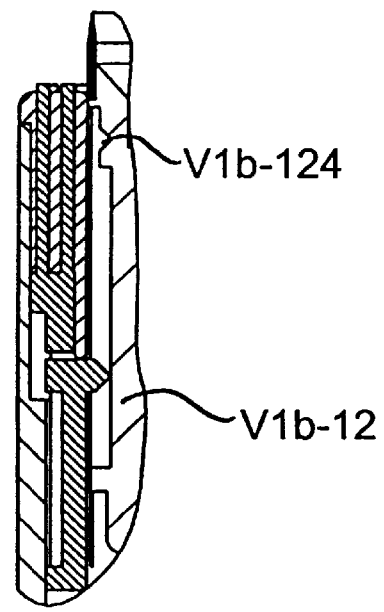

Referring now to FIGS. 10a and 10b it is evident that in the first embodiment variant V1b the scalpel holder V1b-12 is connected to the staple ejector V1b-16 via at least one tab V1-19 in the form of a flexible finger. This tab V1b-19 engages a corresponding recess V1b-124 of the scalpel holder V1b-12 and transfers the force during the stapling action from the scalpel holder V1b-12 to the staple ejector V1b-16 (see FIG. 10a).

Once stapling has been implemented, the staple ejector V1b-16 comes up against the staple cartridge: the tabs V1b-19 then being located in a portion of the inner contour 111 of the housing 11 (FIG. 3) in which the tabs V1b-19 can be bent radially outwards. Due to the ramps of the recess V1b-124 the tabs V1b-19 are urged radially outwards, as a result of which the scalpel holder V1b-12 is decoupled from the staple ejector V1b-16. The scalpel holder V1b-12 then travels by itself and implements the excision (see FIG. 10b).

Unlike the linear-sensitive coupling as described above the coupling now to be described with reference to the FIGS. 11a/11b, FIGS. 12a/12b, FIGS. 13a/13b and in FIGS. 14a/14b in the embodiments, identified as variants V2a to V2d, is termed force-sensitive.

In these embodiments too, stapling occurs prior to the excision. Staple ejectors V2a-16, V2b-16, V2c-16 and V2d-16 as well as scalpel holders V2a-12, V2b-12, V2c-12 and V2d-12 respectively are connected to each other via at least one breakaway lock V2a-10, V2b-10, V2c-10 and V2d-10 respectively. During the stapling action the staple ejectors V2a-16, V2b-16, V2c-16 and V2d-16 and the scalpel holders V2a-12, V2b-12, V2c-12 and V2d-12 respectively travel in common.

Figure 11A:
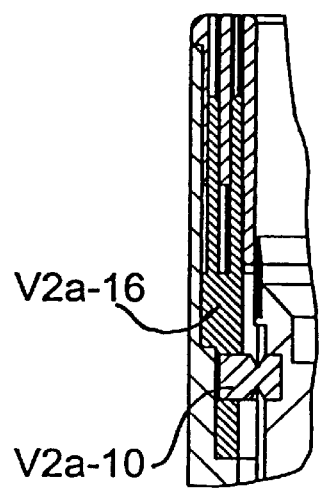
FIGS. 11a and 11b are partial section views of a second embodiment of the scalpel holder and of a staple ejector connected thereto via a coupling element, i.e. shown retracted in FIG. 11a and shown extended in FIG. 11b.
Figure 11B:
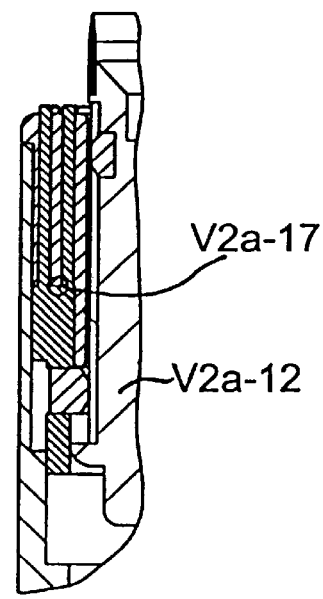

Once the stapling action has been implemented the staple ejector V2a-16, V2b-16, V2c-16 and V2d-16 respectively comes up against the staple cartridge, for example V2a-17 as shown in FIG. 11b. As soon as the stapling force exceeds the breakaway force of the corresponding breakaway lock V2a-10, V2b-10, V2c-10 and V2d-10 respectively the staple ejector V2a-16, V2b-16, V2c-16 and V2d-16 and scalpel holder V2a-12, V2b-12, V2c-12 and V2d-12 respectively decouple so that the latter subsequently travels by itself and implements the excision.

Referring now to FIGS. 11a and 11b there is illustrated a second embodiment (variant V2a) in which the breakaway lock V2a-10 is achieved as a frangible knockout which breaks as soon as the breakaway force is exceeded so that the scalpel holder V2a-12 and staple ejector V2a-16 are subsequently decoupled.

Figure 12A:
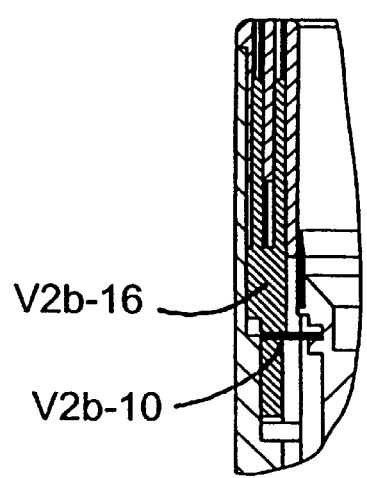
FIGS. 12a and 12b are partial section views of a third embodiment of the scalpel holder and of a staple ejector connected thereto via a coupling element, i.e. shown retracted in FIG. 12a and shown extended in FIG. 12b.
Figure 12B:
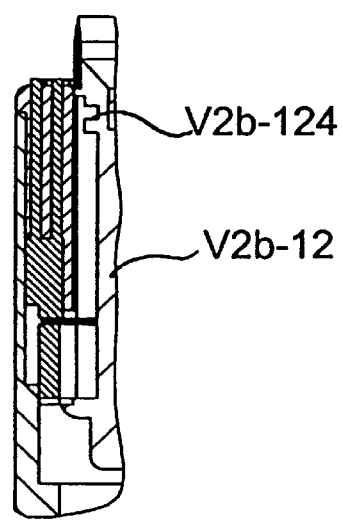

Referring now to FIGS. 12a and 12b there is illustrated a variant V2b in which the breakaway lock V2b-10 is achieved as a leaf spring latch V2b-10 seated in a recess V2b-124 of the scalpel holder V2b-12. When the breakaway force is sufficient the leaf spring latch V2b-10 deforms like a bending finger, causing it to snap out of place from the recess V2b-124, thus resulting in scalpel holder V2b-12 and staple ejector V2b-16 being decoupled from each other.

Figure 13A:
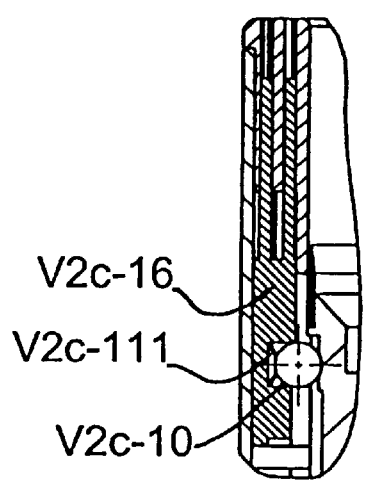
FIGS. 13a and 13b are partial section views of a fourth embodiment of the scalpel holder and of a staple ejector connected thereto via a coupling element, i.e. shown retracted in FIG. 13a and shown extended in FIG. 13b.
Figure 13B:
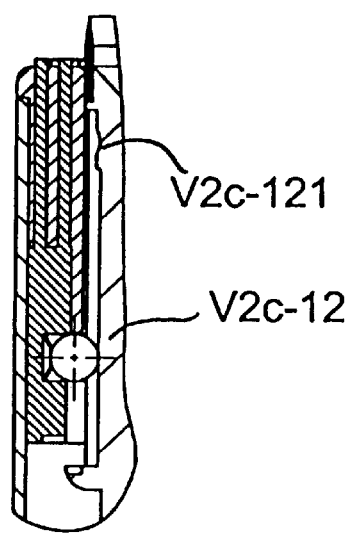

Referring now to FIGS. 13a and 13b there is illustrated a third embodiment (variant V2c) in which the breakaway lock is a ball spring latch, the ball V2c-10 of which is urged by a spring V2c-11 into a recess V2c-121 in the scalpel holder V2c-12. Once the breakaway force on stopping of the staple ejector V2c-16 is sufficient the ball V2c-10 snaps out of place from the recess V2c-121, resulting in the staple ejector V2c-16 being decoupled from the scalpel holder V2c-12.

Figure 14A:
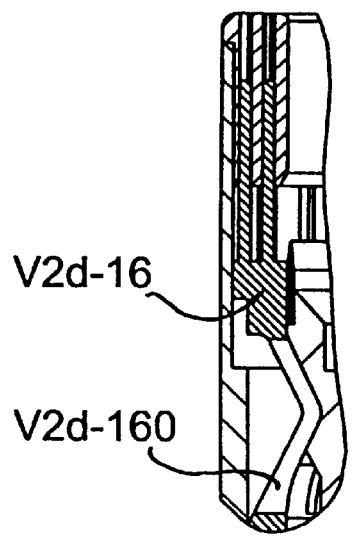
FIGS. 14a and 14b are partial section views of a fifth embodiment of the scalpel holder and of a staple ejector connected thereto via a coupling element, i.e. shown retracted in FIG. 14a and shown extended in FIG. 14b.
Figure 14B:
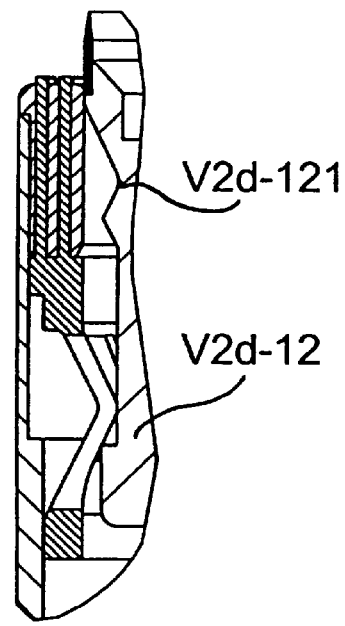

Referring now to FIGS. 14a and 14b there is illustrated a fourth embodiment (variant V2d) in which the coupling element features a corrugated inner contour V2d-160 of the staple ejector V2d-16 engaging a corresponding outer contour V2d-121 of the scalpel holder V2d-12. To decouple the staple ejector V2d-16 from the scalpel holder V2d-12 after the stapling action the breakaway force applied must be sufficient to urge the inner contour V2d-160 of the staple ejector V2d-16 sufficient radially outwards due to the ramp-effect of the outer contour V2d-121 so that the inner contour V2d-160 totally releases from the outer contour V2d-121.

Referring now to FIGS. 15a to 15f there is illustrated a further embodiment of the circular stapling device in the form of a purse string suture applicator. A purse string suture applicator does not serve to directly connect two free ends of a hollow organ, it instead serving to prepare this connection and is thus termed an anastomosis preparator with which a suture loop is applied to a free end of a hollow organ by means of staples.

A purse string suture applicator is configured and functions similarly to the circular stapling device as described above, except that in the purse string suture applicator the staples are not arranged and oriented, as in the stapling device in two rows circumferentially but in one row radially. The remaining configuration of a purse string suture applicator including the scalpel which may be coupled either fixedly to the staple ejector or connected thereto by means of a decoupling mechanism has already been detained in describing the circular stapler.

Likewise, the purse string suture applicator or anastomosis preparator, termed the fifth embodiment (variant V3) in the following comprises the same system connecting the shank tube, the reciprocating driver means as for stapling device described (see V3-112, V3-212, V2-22, V3-23).

A suture loop V3-4 is inserted in a circumferential groove V3-171 in the staple cartridge V3-17 of an instrument head V3-11 and is guided via side groove V3-113 from the instrument head V3-11 to the handle part. The suture loop V3-4 may already be provided with a knot accommodated in a knot holder V3-174.

One end of the hollow organ is drawn via a domed cap V3-31 of a clincher insertion head V3-3 so that the projecting hollow organ comes into contact near to the mandrel V3-2. Subsequently the clincher insertion head is caused to approach the base V3-1 of the instrument head V3-11 until the required staple gap is set, the width of which is checked at the handle.

Stapling is then implemented in which the suture loop V3-4 is attached to the end of the hollow organ by means of radially oriented staples V3-18 and excision of the projection of the hollow organ done by means of a scalpel V3-13. On actuation of a plunger V3-16 the staples V3-18 are ejected by staple ejectors V3-161 from the staple chutes V3-172 of a staple cartridge V3-17 and B-clinched in corresponding staple clinching grooves V3-331 of a metal inlay V3-33. The circular scalpel (annular knife) V3-13 is counterheld in a plastics ring V3-34.

After the stapling action the clincher insertion head V3-3 is again extended from the staple cartridge V3-17 and the hollow organ drawn off with the stapled suture loop. The tissue projection remains on the instrument as a cut-out ring serving to check a correctly implemented loop application.

Referring now to to FIGS. 15a to 15f there is illustrated the embodiment of the purse string suture applicator equipped with gripper arms V3-24 fixedly joined by the mandrel V3-2. The gripper arms V3-24 are open in the distal position of the clincher insertion head V3-2 (see FIGS. 15a, 15d) so that a free end of a hollow organ, for example a free bowel end, may be inserted in the gripper arms V3-24.

When the clincher insertion head V3-3 is moved towards the staple cartridge V3-17, the gripper arms V3-24 close and grip by their ends V3-241 the hollow organ to the groove of the mandrel V2-214. The tissue gap is then set and subsequently the stapling action and excision implemented during which the suture V3-4 is attached to the end of the hollow organ by the staples V3-18 and excision of the projecting tissue done with the circular scalpel V13-13.

Subsequently the clincher insertion head V3-3 is slightly moved away from the staple cartridge V3-17 so that the bowel is easy removed, the radial staple arrangement thereby proving to be no restriction to the extensibility of the bowel, The clincher insertion head V3-3 can be removed by actuating the operating control button V3-36. In addition, the gripper arms V3-24 are configured so that its grippers engage corresponding grooves in the scalpel holder 13, enabling the components to be precisely aligned to each other.

A so-called linear stapling device may be configured in a boom-type form either with a double row of staples and a side-cutting scalpel parallel thereto (see FIGS. 16a to 16d) or with two double rows of staples on both sides of the scalpel (see FIG. 16h), or it may be equipped optionally with a fixedly fitted or attachable purse-string suture staple as evident from, for example, FIGS. 16e to 16g. The connections to the operating control part configured as the "handle part" are configured analogously. A linear stapling device serves to undertake closures on hollow organs.

Referring now to FIGS. 16a to 16h there is illustrated a fifth embodiment (variant V4) in which a anvil V4-3 is fixedly connected to the mandrel (V4-2) by means of the handle part during coarse and fine adjustment, the mandrel comprising at its distal end slots V4-212. This connection is non-releasable during a stapling action and can be only be separated with the clincher insertion head V4-3 extended.

A staple cartridge V4-17 is fixedly connected to a base part V4-1 (FIG. 16d) which is coupled to a shank tube (not shown in FIG. 16) of the handle part via push button fastener V4-112. An ejector V4-16 is shiftingly mounted in the head unit housing V4-11 and coupled to a pusher (likewise not shown) in the handle part.

The ejector V4-16 ejects by plungers V4-161 the staples V4-18 from the staple chutes V4-172 of the staple cartridge V4-17. The staples V4-18 are B-clinched in corresponding clinching grooves V4-331 in a metal inlay V4-33 (FIG. 16f) of the clincher insertion head V4-3 whilst a linear scalpel V4-13 configured optionally fixed or releasably coupled to the ejector V4-16 is guided in the scalpel groove V4-173 to part the hollow organ and to cut into a plastics body V4-34.

Referring now to FIGS. 16e to 16g there is illustrated a further embodiment of a linear stapler including a linear scalpel and a single-sided double staple suture with which a corrugated clamping of the bowel may be achieved by corresponding purse-string suture staples V4-19 and V4-38 on the other side facing away from the staple side. In this arrangement the hollow organ is located in a corrugated position in the recesses V4-191 and V4-381. Prior to implementing the staple stitching action a suture V4-4 is guided towards the side of the clincher insertion head and back to the staple cartridge (or vice-versa) via two suture guide grooves V4-192 and V4-382 oriented parallel to the knife. In this way a purse-string suture loop may be directly placed with needle and filament through the tissue.

A linear boom-type stapling device is made use of to produce a closure in a hollow organ by a two-row stapling action and the projecting tissue trimmed with a knife. Referring now to FIGS. 17a to FIG. 17g there is illustrated an embodiment with which a linear double row of staples V5-172 may be placed on one side of the linear scalpel V5-13.

Furthermore, a double row of staples may also be placed on each side of the linear scalpel (see FIG. 16h). By means of the linear scalpel a closed hollow organ may be parted by a cut between the two double rows of staples thus resulting in two closed hollow organ stubs.

In a further aspect (not shown) of a linear stapler including a linear scalpel and a double row of staples on one side a corrugated clamp of the bowel may be achieved on the other side of the linear scalpel, i.e. facing away from the staple side. Before implementing the stapling stitching action a suture may be applied with the needle guided towards the clincher insertion head and back to the the staple cartridge (or vice-versa) via two suture guide grooves oriented parallel to the knife thus resulting in a purse-string suture stitch being directly placed through the tissue (see FIGS. 16e to 16g).

An alligator-type linear stapling device consists of a fixed base part V5-1 to which the staple cartridge V5-17 is fixedly connected and in which ejector and scalpel holder V5-16 as well as pusher V5-12 are shiftingly mounted with a locating pin. The clincher insertion head V5-3 with the staple clinching grooves V5-331 and a plastics inlay V5-34 serving as the cutting surface area for the annular knife V5-15 is movably mounted in the head unit housing V5-11 via a pin joint V5-313 in a guide V5-114.

Figure 17A:
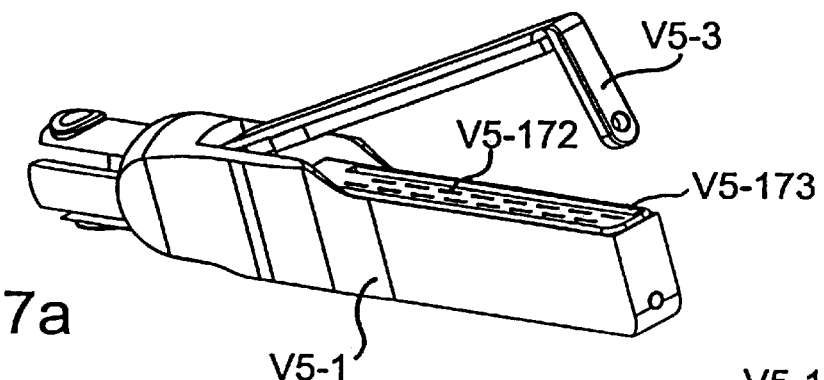
FIG. 17a is a perspective illustration of a second embodiment of a linear stapler with the pusher open.
Figure 17B:
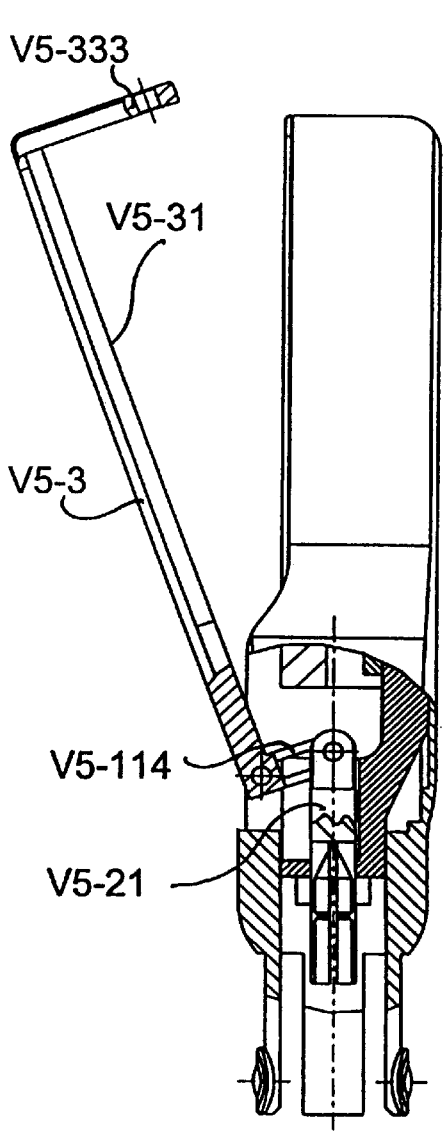
FIG. 17b is a side view of the linear stapler as shown in FIG. 17a shown partly in section with the pusher open and stapling implemented.
Figure 17C:
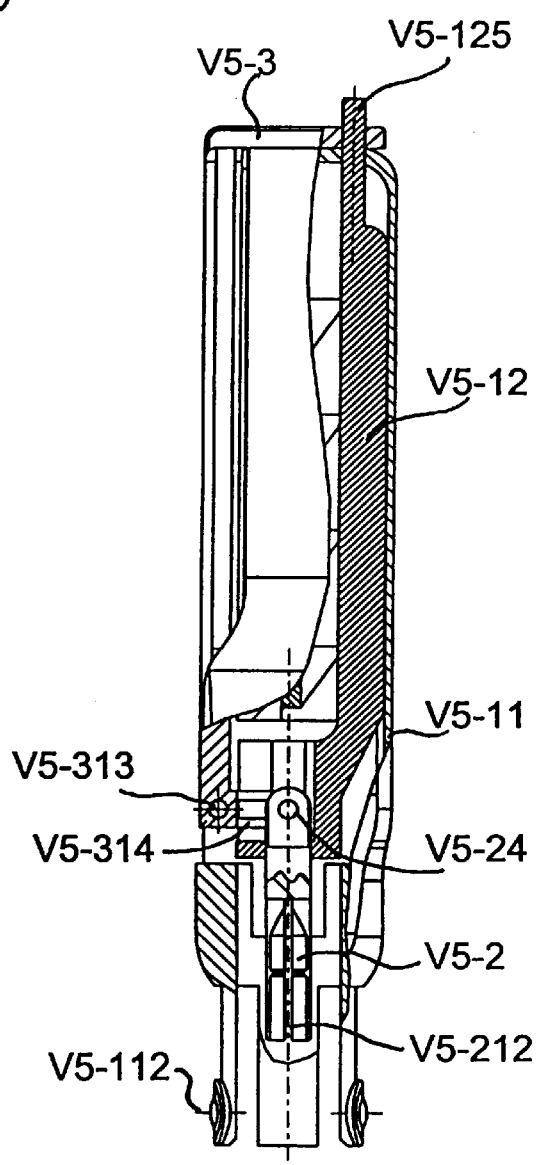
FIG. 17c is a side view of the linear stapler shown partly in section with the pusher closed and stapling implemented.
Figure 17D:
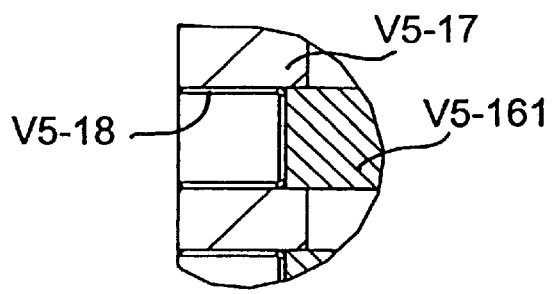
FIG. 17d is a detail illustration of the staple cartridge of the linear stapler as shown in 17e shown partly sectioned.
Figure 17G:
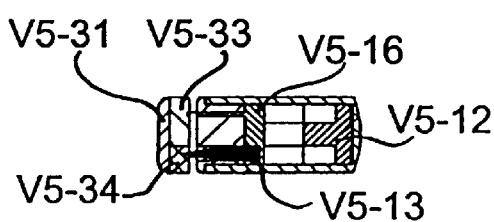
FIG. 17g is a section view taken along the line 17g—17g as shown in FIG. 17f.
Figure 17E:
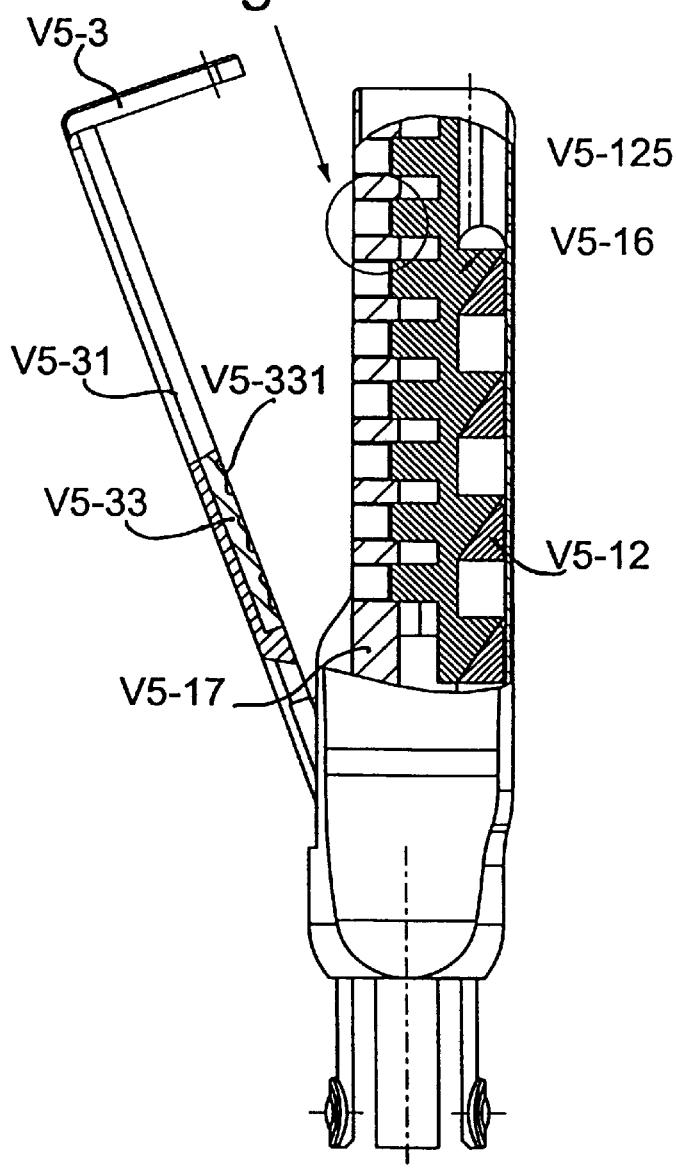
FIG. 17e is a view of the linear stapler as seen from above with the pusher open.
Figure 17F:
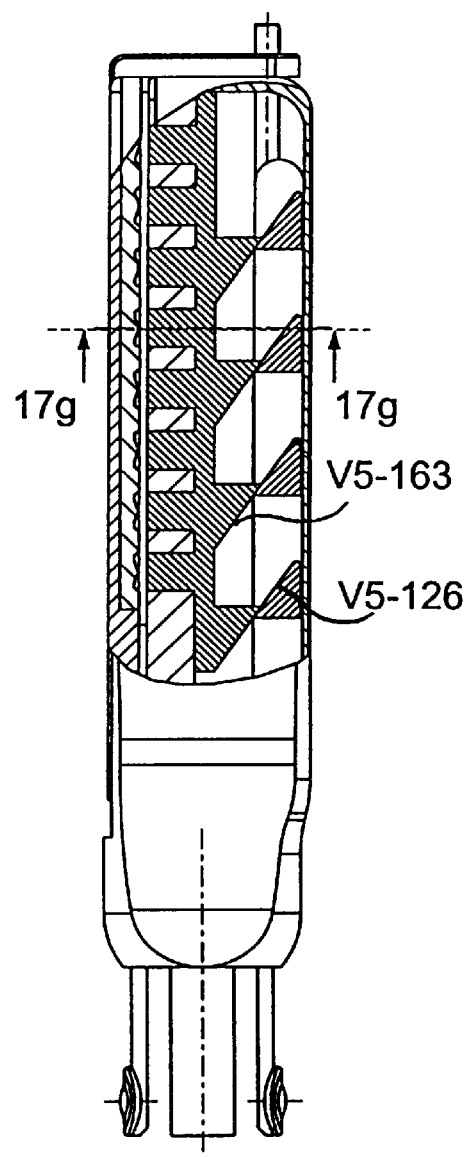
FIG. 17f is a perspective illustration of the linear stapler corresponding to that as shown in FIG. 17e with the pusher closed and stapling implemented.

Referring now to FIGS. 17e and 17f there is illustrated an ejector V5-16 guided via staple ejectors V-161 in staple chutes V5-172 of the staple cartridge V5-17 has ramps V5-163 via which it is actuated by the pusher V5-12 via corresponding ramps V5-126. Additionally secured to the ejector is a linear scalpel V5-13 which is guided in a groove V5-173 in the cartridge V5-17, whereby knife and ejector may be actuated partly decoupled from each other.

Referring now to FIGS. 17c and 17f there is illustrated how the anvilV5-31 may be optionally fitted at its distal end with a latching hole V5-333 engaged by a locating pin V5-125 so that the clincher insertion head is not deformed during clinching of the staples V5-18 and cutting, i.e. retains its desired position.

The connection to a "handle part and shank tube" is configured the same as in the other head units. The base is fixedly connected via the push button fastener V5-112 but relesably connected to the shank tube. Preventing release during a stapling action is achieved by the snap-action noses of the push button fastener V5-112 being locked in place by a stop to prevent accidental opening.

The clincher insertion head V5-31 is driven in a connecting link V5314 from the mandrel V5-21 via a toggle pin V5-24 which is coupled to the inner pusher medium of the "handle part" via a resilient connector V5-212 and is likewise locked in place to prevent accidental release during the stapling action. The ejector V5-16 is actuated by the pusher with the locating pin V5-12 which is connected to the outer pusher medium of the handle part.

Opening and closing the clincher insertion head is thus achieved by actuating a coarse and vernier adjustment on the handle part whilst locking the clincher insertion head in place and implementing stapling is controlled by a toggle handle provided on the handle part.

The alligator-type linear stapler is intended for application in minimally invasive surgery since due to its small cross-section there is no problem in introducing it through a trocar.

Referring now to FIGS. 18a to 18d there is illustrated an anastomosis applicator permitting application of an anastomosis ring V6-5 (e.g. a VALTRAC" ring). The anastomosis ring V6-5 is mounted in the open condition (see V6-51 in FIG. 18b) on an annular gripper V6-19 and locked in place by means of a clamping device V6-2. The clamping device V6-2 comprises a conical section V6-25 of a mandrel V6-21 which expands the annular gripper and arrests the anastomosis ring V6-5 relative to a ring mount V6-11 of a base part V6-1.

The instrument is then introduced into the hollow organ stub, for example via side incision, until the distal ring-half protrudes from the previously freely prepared end of the hollow organ provided with a purse-string suture loop.

By tightening the purse-string suture in the annular gripper and knotting, the first end of the hollow organ is defined in the gap between the halves of the anastomosis ring. Then, the second free end of the bowel is tightened with the purse-string suture via the distal ring-half and likewise defined on the ring by the suture loop.

After this, by actuating the handle part and the resulting movement of an ejector V6-16 the proximal ring-half is moved from the ejector V6-16 onto the distal ring-half until the ring-halves interlock. Subsequently, the mandrel V6-21 is moved over a short distance distally, thus resulting in the closed anastomosis ring (see condition V6-52 as shown in FIG. 18d) being released from the mandrel to enable the instrument to be removed from the hollow organ.

As in the other head variants the connection to the handle part and shank tube is configured analogously to that of the circular stapler. The mandrel V6-21 is connected to the head adjuster via a resilient connection in the form of a snap-action nose connection V6-212. The expanding mandrel is part of the base part V6-1 to which also a funnel-clinched ring cover V6-11 is joined in which the ring is circumferentially guided. The base part is connected to the shank tube via snap-action nose connection V6-112. The ejector V6-16 which closes the anastomosis ring is connected to the middle pusher medium and is actuated by the toggle handle.

What is claimed is:

1. An apparatus for connecting a variety of surgical instruments to an operating control device including a handle part and a shank part wherein for connecting a surgical instrument to the distal end of a shank part of said operating control device a push-button fastener (112) is provided at the proximal end of said instrument, and for connecting and actuating the function elements (12, 13, 16, 17) of said instrument a mandrel assembly (2, V3-2, V4-2, V5-2, V6-2) is provided at the proximal end of said instrument, said mandrel assembly being mounted on and latched to a receiving part (43, 44) at the distal end of an adjuster mechanism actuated by said operating control means.

2. The apparatus as set forth in claim 1 wherein said mandrel assembly (2) is a tubular pin body (21) slotted at the proximal end with spline portions (22, 23) mounted on and latched to a contact pin (43) guided and positioned in said shank part and connected to said adjuster mechanism.

3. Use of the apparatus as set forth in claim 1 for connecting a variety of surgical instruments for minimally invasive surgery (MIS).

4. Use of the apparatus as set forth in claim 1 for connecting a variety of surgical instruments for open surgery.

5. The apparatus as set forth in claim 1 for a surgical MIS instrument in the form of a stapling device comprising a scalpel holder, a circular scalpel, a staple cartridge with staples accommodated therein and a staple ejector assigned to said staples and a clincher insertion head wherein for simultaneously implementing a stapling action and excision said scalpel holder (V1a-12) and said staple ejector (V1a-16) are axially shiftable as a fixedly coupled assembly.

6. The apparatus as set forth in claim 1 for a surgical MIS instrument in the form of a stapling device comprising a scalpel holder, a circular scalpel, a staple cartridge with staples accommodated therein and a staple ejector assigned to said staples and a clincher insertion head wherein said scalpel holder (V2a-12) and staple ejector (V2a-16) are coupled axially shiftable in such a way that following implementation of a stapling action said scalpel holder (V2a-12) and said staple ejector (V2a-16) are decoupled and subsequently said scalpel holder (V2a-12) is travelled so that an excision is implemented by means of said scalpel.

7. The apparatus as set forth in claim 6 wherein a flexible part (V2d-160) is provided as said coupling and decoupling element between scalpel holder (V2d-12) and staple ejector (V2d-16).

8. The apparatus as set forth in claim 6 wherein a breakaway lock (V2a-10, V2b-10, V2c-10, V2d-160) is provided as said coupling and decoupling element, said breakaway lock decoupling said scalpel holder (V2a-12) and said staple ejector (V2a-16) on the breakaway force being exceeded.

9. The apparatus as set forth in claim 8 wherein said breakaway lock is configured as a frangible knockout (V2a-10).

10. The apparatus as set forth in claim 8 wherein said breakaway lock is configured as a leaf spring latch (V2b-10).

11. The apparatus as set forth in claim 8 wherein said breakaway lock is configured as a ball spring latch (V2c-10, V2c-111).

12. The apparatus as set forth in claim 8 wherein for coupling and decoupling, a corrugated inner structure (V2d-160) at said staple ejector (V2d-16) cooperates with a corresponding outer contour (V2d-121) of said scalpel holder (V2d-12) by means of a ramp effect.

13. The apparatus as set forth in claim 1 for a surgical MIS instrument in the form of a purse-string suture applicator including a scalpel holder, a circular scalpel, a staple cartridge with staples accommodated therein, a staple ejector and a clincher insertion head wherein a number of resilient gripper elements (V3-24) for holding one end of a hollow organ for preparation being fixedly connected to said mandrel assembly (V3-2), said staples (V3-18) being accommodated radially oriented in said staple cartridge (V3-17) and a suture loop (V3-4) being inserted in a circumferential groove (V3-171) of said staple cartridge (V3-17).

14. The apparatus as set forth in claim 13 wherein said suture loop (V3-4) is provided with a knot accommodated in a knot holder (V3-174).

15. The apparatus as set forth in claim 1 for a surgical MIS instrument in the form of a linear stapling device including a scalpel holder, a linear scalpel, a staple cartridge with staples accommodated therein, a staple ejector and a clincher insertion head wherein said linear stapler oriented in the direction of said shank part axis comprises a base part (V5-1) to which said staple cartridge (V5-17) is fixedly coupled, in which said staple ejector and said scalpel holder (V5-16) including said linear scalpel (V5-13) as well as a pusher with locating pin (V5-12) are shiftingly mounted and on which a clincher insertion head (V5-31) with staple clinching grooves is pivotably mounted.

16. The apparatus as set forth in claim 15 wherein said staple ejector (V5-16) comprises on the side facing away from said clincher insertion head (V5-3) ramped sections (V5-126) actuatable via corresponding ramped sections (V5-163) provided at said pusher (V5-12).

17. The apparatus as set forth in claim 1 for a surgical MIS instrument in the form of an anastomosis applicator including an anastomosis ring wherein for closing said anastomosis ring (V6-5) and for releasing said closed anastomosis ring from said anastomosis applicator an anular gripper (V6-19) and a clamping device (V6-21, V6-25) assigned thereto actuated by said handle part to define and clamp two ends of a hollow organ each provided with a purse-string suture on both halves of said anastomosis ring (V6-5) and an ejector (V6-16) and a mandrel (V6-21) mountable on said mandrel assembly (2), likewise actuatable from said handle part, are provided.

18. The apparatus as set forth in claim 1 for an instrument applicable in open surgery, in the form of a linear stapling device including a scalpel holder, a linear scalpel, a staple cartridge with staples accommodated therein and a staple ejector assigned to said staples and a clincher insertion head wherein said staples (V4-18) are accommodated in staple chutes (V4-172) arranged in a double row of said staple cartridge (V4-17) and said linear scalpel (V4-13) provided parallel to said staple cartridge (V4-17) is sensed fixedly or releasably coupled to said staple ejector (V4-16, V4-161).

19. The apparatus as set forth in claim 15 wherein on the side of said linear scalpel (V4-13) facing away from said staple cartridge (V4-17) corresponding purse-string staples (V4-19, V4-38) are provided for a corrugated clamping of one end of a hollow organ, suture guide grooves (V4-191 and V4-391) oriented parallel to said linear scalpel (V4-13) being configured at said purse-string staples (V4-19, V4-38).

\* \* \* \* \*